US006702741B2

(12) United States Patent
Rioux et al.

(10) Patent No.: US 6,702,741 B2
(45) Date of Patent: *Mar. 9, 2004

(54) MEDICAL BODY ACCESS DEVICE

(75) Inventors: Robert F. Rioux, West Bridgewater, MA (US); Raymond Rackley, Shaker Heights, OH (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/198,856

(22) Filed: Jul. 19, 2002

(65) Prior Publication Data

US 2002/0183595 A1 Dec. 5, 2002

Related U.S. Application Data

(63) Continuation of application No. 09/296,829, filed on Apr. 22, 1999, now Pat. No. 6,450,952.
(60) Provisional application No. 60/082,718, filed on Apr. 23, 1998.

(51) Int. Cl.[7] .................................................. A61B 1/32
(52) U.S. Cl. ........................................ 600/233; 600/225
(58) Field of Search ............................ 600/184, 185–246

(56) References Cited

U.S. PATENT DOCUMENTS

| 424,140 A | 3/1890 | Shuford |
| 439,028 A | 10/1890 | Washington |
| 458,708 A | 9/1891 | Daily ........................ 600/225 |
| 471,990 A | 3/1892 | Daily ..................... 600/225 X |
| 605,652 A | 6/1898 | Pitt ........................ 600/225 X |
| 847,542 A | 3/1907 | Barber ........................ 600/225 |
| 870,021 A | 11/1907 | Duffee |
| 1,246,340 A | 11/1917 | Smit ....................... 600/225 X |
| 1,358,473 A | 11/1920 | Smith |
| 2,253,132 A | 8/1941 | Malson ........................... 32/63 |
| 2,320,709 A | 6/1943 | Arnesen ....................... 128/17 |
| 2,400,251 A | 5/1946 | Nagel ......................... 128/361 |
| 2,575,253 A | 11/1951 | Bicek ............................. 128/3 |
| 2,592,190 A | 4/1952 | Rubens et al. .......... 600/225 X |
| 2,631,585 A | 3/1953 | Siebrandt .................... 606/205 |
| 2,751,903 A | 6/1956 | Ivory et al. ................... 128/20 |
| 2,809,628 A | 10/1957 | Jonas ........................... 128/17 |
| 2,829,649 A | 4/1958 | Glenner ....................... 128/325 |
| 2,844,144 A | 7/1958 | Massey ...................... 128/131 |
| 2,858,826 A | 11/1958 | Kahn ........................... 128/17 |
| 3,551,987 A | 1/1971 | Wilkinson ................... 29/212 |

(List continued on next page.)

FOREIGN PATENT DOCUMENTS

| BR | PI 7905185 | 2/1981 |
| CH | 273 809 | 6/1951 |
| EP | 0407357 | 1/1991 |
| FR | 1 594 869 | 7/1970 |

(List continued on next page.)

OTHER PUBLICATIONS

Copy of International Search Report.
Mitchell, "Hook Needle and Retractor for Posterior Urethroplasty." British Journal of Urology 42: 599–600 (1970).

*Primary Examiner*—Kevin Shaver
*Assistant Examiner*—Candice C. Melson
(74) *Attorney, Agent, or Firm*—Testa, Hurwitz & Thibeault, LLP

(57) ABSTRACT

A medical device for retracting tissue allows access to the inside of the body by "prying open" an existing or created opening in a body. The device comprises a substantially transparent head having first and second head halves defining a substantially conical surface including a gap when the first and second head halves are joined. Angular motion of the first and second head halves enlarges the existing or created opening and provides an area of access to the inside of the body. The substantially transparent nature of the device allows it to function as a light pipe so that the operator can see the body cavity or tract opened by the device. The device has scissors-like handles to allow an operator to open or close the device with one hand.

10 Claims, 13 Drawing Sheets

U.S. PATENT DOCUMENTS

| | | | | |
|---|---|---|---|---|
| 3,575,163 A | 4/1971 | Gaspar | | 128/17 |
| 3,709,215 A | 1/1973 | Richmond | | 128/20 |
| 3,744,481 A | 7/1973 | McDonald | | 128/6 |
| 3,745,992 A * | 7/1973 | Poirier | | 600/225 |
| 3,750,651 A | 8/1973 | Brammer | | 128/20 |
| 3,752,149 A | 8/1973 | Ungar et al. | | 128/12 |
| 3,762,400 A | 10/1973 | McDonald | | 128/18 |
| 3,789,835 A | 2/1974 | Whitman | | 128/18 |
| 3,796,214 A | 3/1974 | Davis | | 128/20 |
| 3,817,242 A | 6/1974 | Uddenberg | | 128/20 |
| 3,841,318 A | 10/1974 | Olson | | 128/20 |
| D245,515 S | 8/1977 | Troutner et al. | | D24/29 |
| 4,085,756 A | 4/1978 | Weaver | | 128/303.17 |
| 4,156,424 A | 5/1979 | Burgin | | 128/18 |
| 4,206,750 A | 6/1980 | Kaivola | | 128/17 |
| 4,254,763 A | 3/1981 | McCready et al. | | 128/20 |
| 4,263,898 A | 4/1981 | Wannag | | 128/17 |
| 4,300,541 A | 11/1981 | Burgin | | 128/18 |
| 4,323,057 A | 4/1982 | Jamieson | | 128/17 |
| 4,432,351 A | 2/1984 | Hoary | | 128/17 |
| D274,356 S | 6/1984 | Riedell | | D24/18 |
| D275,790 S | 10/1984 | Marlowe | | D24/27 |
| 4,502,468 A | 3/1985 | Burgin | | 600/212 |
| 4,562,832 A | 1/1986 | Wilder et al. | | 128/20 |
| 4,638,792 A | 1/1987 | Burgin | | 128/6 |
| 4,766,887 A | 8/1988 | Cecil, Jr. et al. | | 128/17 |
| D299,532 S | 1/1989 | Cecil, Jr. et al. | | D24/29 |
| 4,813,401 A | 3/1989 | Grieshaber | | 128/20 |
| 4,854,300 A | 8/1989 | Corbo | | 128/17 |
| 4,945,897 A | 8/1990 | Greenstein | | 128/20 |
| 5,026,376 A | 6/1991 | Greenberg | | 606/96 |
| D319,877 S | 9/1991 | O'Neal-Cox | | D24/143 |
| 5,072,720 A | 12/1991 | Francis et al. | | 128/17 |
| 5,122,130 A | 6/1992 | Keller | | 606/61 |
| 5,165,387 A | 11/1992 | Woodson | | 128/6 |
| 5,174,278 A | 12/1992 | Babkow | | 128/17 |
| 5,179,937 A | 1/1993 | Lee | | 128/17 |
| 5,231,973 A | 8/1993 | Dickie | | 128/17 |
| 5,237,985 A | 8/1993 | Hodgson | | 128/17 |
| 5,308,349 A | 5/1994 | Mikhail | | 606/88 |
| 5,377,667 A | 1/1995 | Patton et al. | | 128/3 |
| 5,397,330 A | 3/1995 | Mikhail | | 606/88 |
| 5,465,709 A | 11/1995 | Dickie et al. | | 600/223 |
| 5,536,251 A | 7/1996 | Evard et al. | | 604/93 |
| 5,618,260 A | 4/1997 | Caspar et al. | | 600/210 |
| 5,681,265 A | 10/1997 | Maeda et al. | | 600/219 |
| 5,782,865 A | 7/1998 | Grotz | | 606/232 |
| 5,785,640 A | 7/1998 | Kresch et al. | | 600/29 |
| 5,785,648 A | 7/1998 | Min | | 600/220 X |
| 5,865,729 A | 2/1999 | Meehan et al. | | 600/207 |
| 5,873,820 A | 2/1999 | Norell | | 600/220 |
| 6,059,723 A | 5/2000 | Davis | | 600/241 |
| 6,258,024 B1 | 7/2001 | van Der Weegen | | 600/115 |

FOREIGN PATENT DOCUMENTS

| | | |
|---|---|---|
| FR | 2158962 | 6/1973 |
| FR | 2610507 | 8/1988 |
| FR | 2693098 | 1/1994 |
| GB | 1462929 | 1/1977 |
| GB | 1477227 | 6/1977 |
| GB | 2128094 | 4/1984 |
| WO | WO 94/12091 | 6/1994 |
| WO | WO 95/13009 | 5/1995 |
| WO | WO 95/31131 | 11/1995 |
| WO | WO 96/28083 | 9/1996 |
| WO | WO 97/01983 | 1/1997 |
| WO | WO 97/43982 | 11/1997 |

* cited by examiner

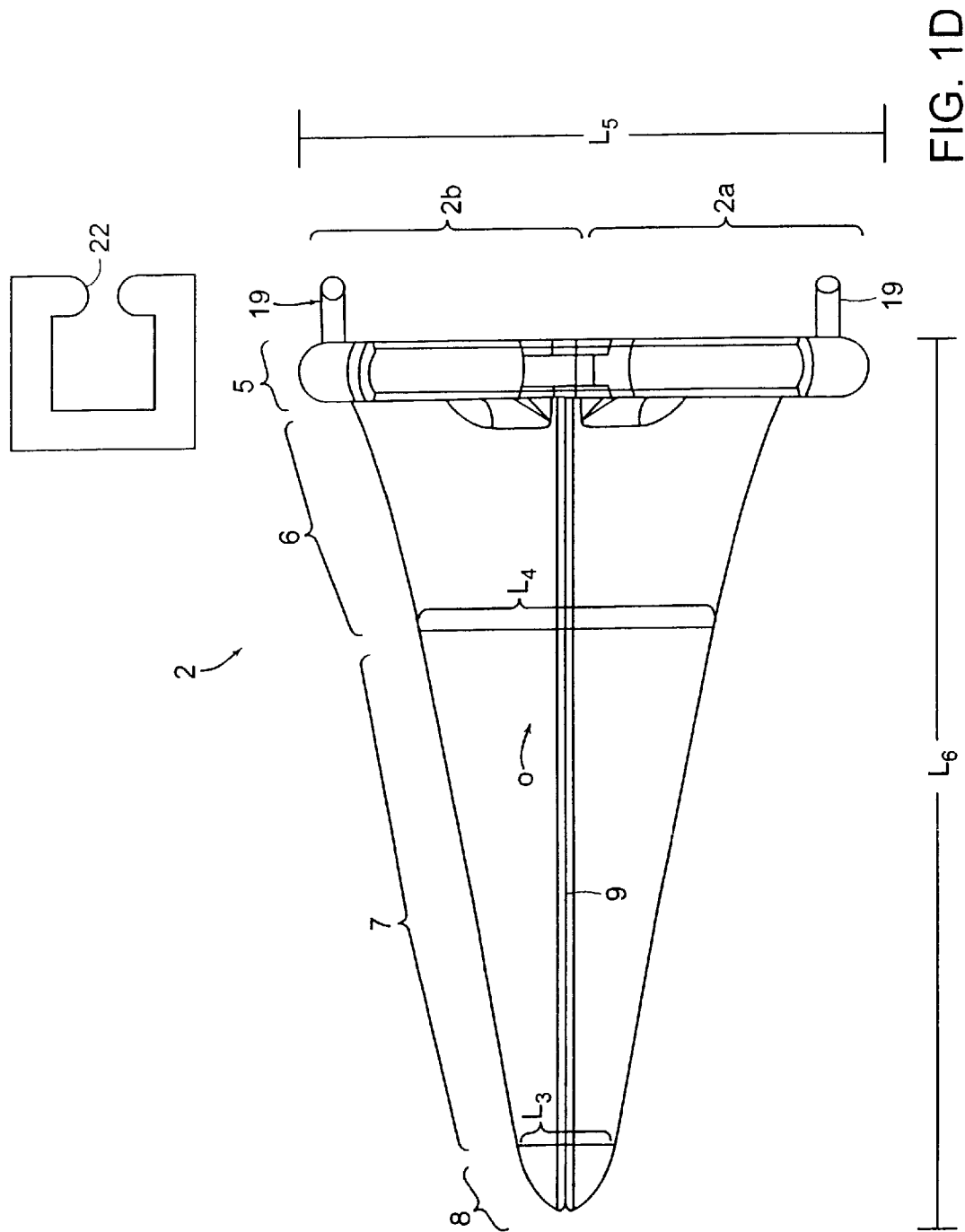

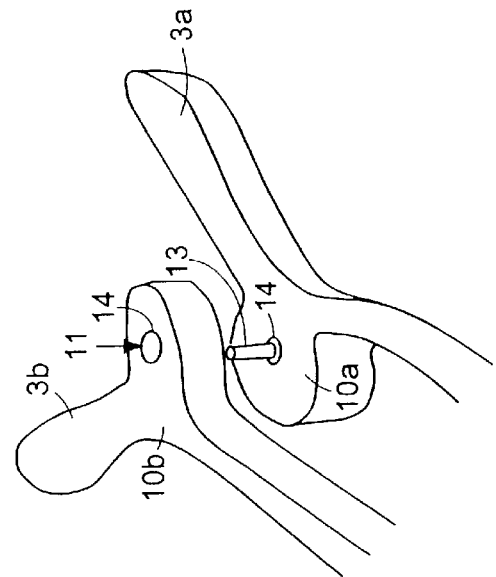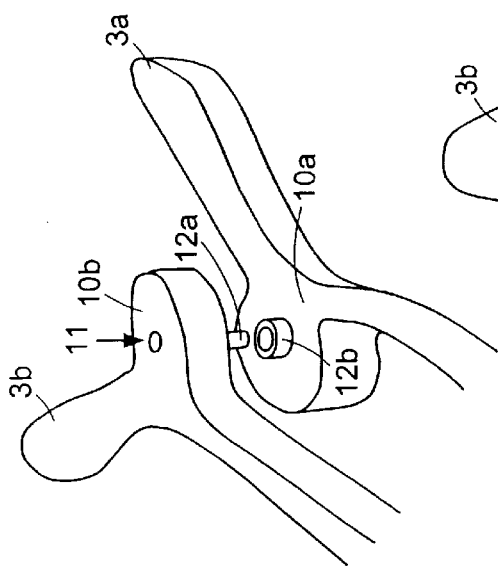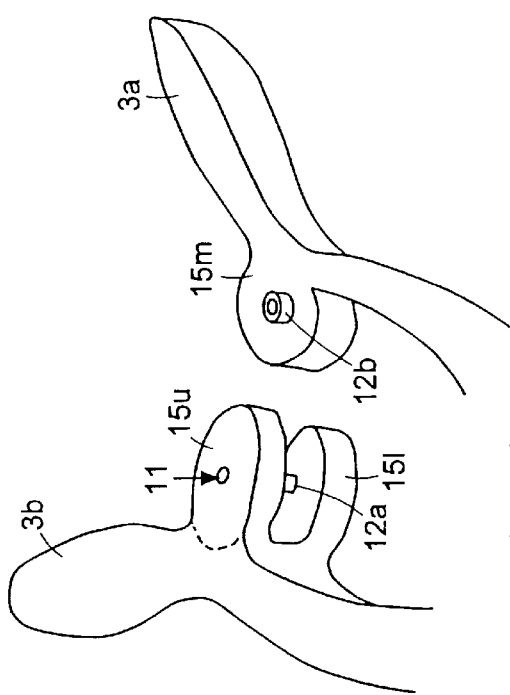
FIG. 6A
FIG. 6B
FIG. 6C

MEDICAL BODY ACCESS DEVICE

CROSS-REFERENCE TO RELATED APPLICATIONS

This application is a continuation of U.S. Ser. No. 09/296,829, filed Apr. 22, 1999, now U.S. Pat. No. 6,450,952, which claims benefit of U.S. Provisional Patent Application No. 60/082,718, filed Apr. 23, 1998, the contents of each of which are incorporated herein by reference.

TECHNICAL FIELD

This invention relates to a medical device that allows access to the inside of the body by "prying open" an existing or created opening in a body.

BACKGROUND INFORMATION

Medical devices for retracting tissue are generally referred to as retractors or specula. A retractor typically is used to draw aside the edges of a wound or opening (e.g., to separate and hold open the rib cage of a patient) or to hold back structures adjacent an operative field. A speculum typically is used to enlarge the opening of any canal or cavity (e.g., the vagina or the rectum) to facilitate inspection of the interior of the canal or cavity.

Typically, levers or handles of retractors and specula are disposed in the line of sight of the body cavity in which the device is inserted thus interfering with an operator's (e.g., a physician's) ability to examine and view the cavity and to properly place medical instruments into the cavity.

Retractors and specula also typically limit or prevent tactile access. That is, an operator typically cannot insert a hand or a finger into the body opening being held or forced open by the device.

Retractors and specula are typically made of steel, causing discomfort to the patient. Improper sterilization and repeated use of these instruments also increases the risk of infection.

SUMMARY OF THE INVENTION

This invention relates to a medical retractor/speculum device for vaginal or other applications that allows access to the inside of the body by "prying open" an existing or created opening in a body. The device has scissors-like handles to allow an operator to open or close the device with one hand. In one embodiment of the invention, the device has a locking mechanism to allow the device to stay closed, open, or partially open, as placed by the operator with one hand.

In one embodiment of the invention, a medical device for retracting a body opening comprises a substantially transparent head coupled to a handle. The head comprises a first head half and a second head half which together define a substantially conical surface including a gap when the first head half and second head half are joined. The handle is coupled to the wider base of the head and comprises two handle portions that can be joined at a common hinge or pivot point. The handle portions can be manipulated like the handles of a pair of scissors. Actuation of the handle by bringing the handle portions together causes angular motion of the first head half and the second head half relative to a longitudinal axis of the head, exerting a retraction force on the body opening, thereby enlarging the body opening. Actuation also enlarges the gap in the head so as to provide the operator with an area of access to the inside of the body opening through the gap.

The increase in the size of the gap upon actuation of the handle allows the operator to insert at least a finger, and preferably most of the hand up to the knuckles, into the segment of the head which extends outside of the body opening. This allows the operator the ability to touch the inside of the body opening being retracted and to identify structure(s) within the body opening. As the handle portions can be manipulated with a single hand, the other hand of the operator is free to examine the patient.

In some embodiments of the invention, a longitudinal axis of the handle is substantially perpendicular to the longitudinal axis of the head, and the handle is disposed out of the line of sight of the body cavity. Also, the retractor/speculum device can be configured to include a light source or to receive one or more light-transmitting fibers or cables. The light will illuminate at least the substantially transparent head of the device to provide illumination of the retracted area. The device of the invention allows transvaginal surgical procedures to proceed more quickly and safely than when other known devices are used. One-hand operation of the device is possible, in accordance with the invention.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIGS. 1A–D show perspective views of a retractor/speculum device in a closed position according to one embodiment of the invention. FIG. 1A is perspective view from the top of the device showing the gap formed between the two halves of the head of the device. FIG. 1B is a perspective view from the side and back of the device showing the gap formed between the two halves of the head. FIG. 1C is perspective view of the back of the device. FIG. 1D is a view of the bottom of the head of the retractor/speculum of FIG. 1.

FIG. 2A is a perspective view from the side and back of the device showing the enlarged gap formed between the two halves of the head of the device. FIG. 2B is a perspective view of the back of the device.

FIGS. 6A–C show enlarged views of hinge assembles according to different embodiments of the invention.

DESCRIPTION

Figure 7:
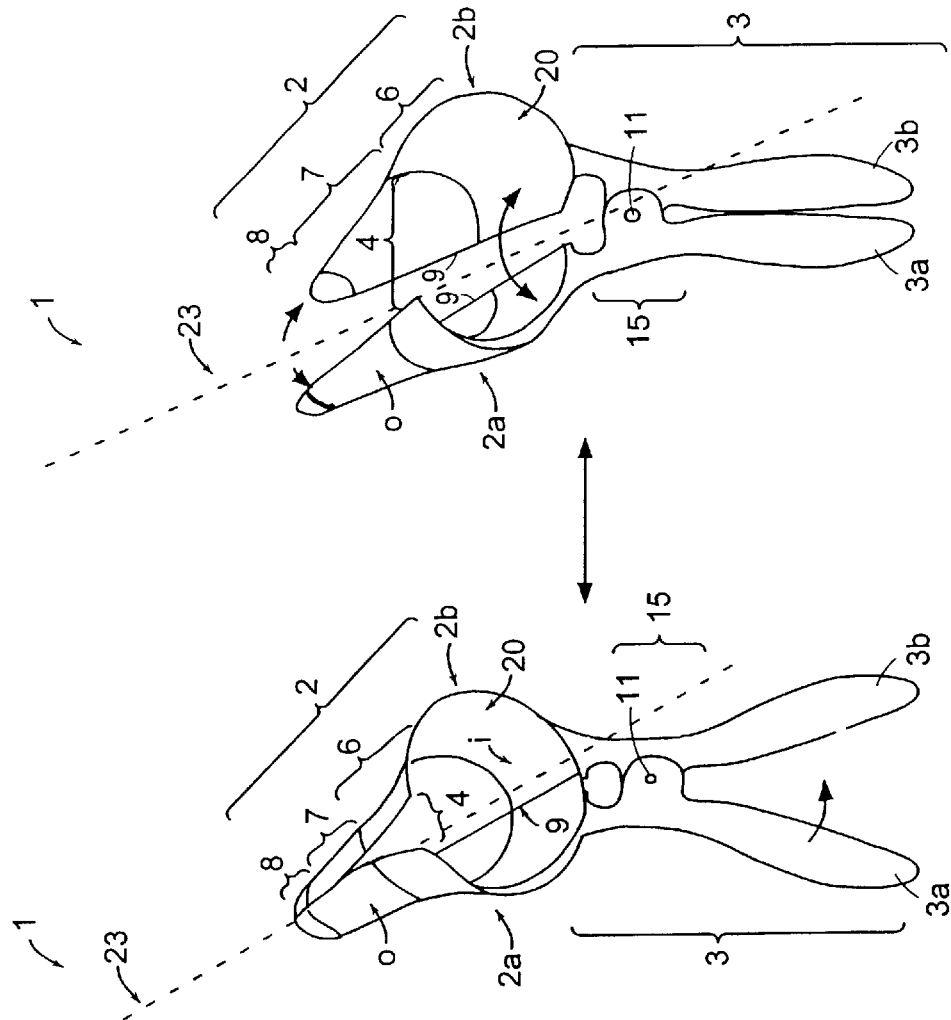
FIG. 7 shows a schematic diagram of the movement of each head half of the retractor/speculum device upon actuation of the handle. The left side of the figure shows the device in a closed configuration. The right side of the figure shows the device in an open configuration.

A device according to the invention is useful for retraction and functions as a medical retractor and/or speculum. As shown in FIGS. 1A–D, 2A–B, 3A–B, 4A, 5A–B, and 7, the device 1 comprises a head 2 and a handle 3. In a disclosed embodiment, both the head 2 and handle 3 comprise two substantially symmetrical halves (first head half 2a and second head half 2b, and handle portions 3a and 3b, respectively) which are generally mirror images of each other. As shown in FIG. 7, the two halves 2a and 2b of the head 2 are capable of angular motion relative to a longitudinal axis 23 of the head 2 upon actuation or manipulation of the handle 3, moving away from each other through an arcuate path when the device is being "opened" to exert a retraction force, and moving toward each other when the device is being "closed."

The device 1 can be made of a substantially transparent thermoplastic material that transmits light, such as polycarbonate (e.g., Lexan OQ®, Flexlite Corporation, Boca Raton, Fla.), acrylic, or polystyrene, although any type of material that can resist the retraction force of the area being retracted and that can transmit light when illuminated can be used. The device 1 may be entirely substantially transparent or the head 2 alone may be substantially transparent. A substantially transparent material is intended to include any material that can transmit light.

While any type of material can be used that can resist the retraction force of the area being retracted and that can transmit light when illuminated by a light source, plastic has several advantages as a material for the retractor/speculum device 1 (or the head 2 alone) of the invention. As an example, a plastic device 1 is disposable and provides a single-use medical instrument that helps to eliminate the occurrence of cross-infection typically associated with improperly sterilized multi-use metal instruments. Also, because plastic has a lower coefficient of thermal conductivity than steel or metal, the patient experiences less discomfort as the retractor/speculum device 1 of the invention feels warmer and more comfortable to the patient. Moreover, the use of a substantially transparent material, such as clear plastic, results in a device 1 that acts as a light pipe. The need for another operator or assistant to hold a separate light source is eliminated because a light source, or fiber optic lines carrying light from a light source, can be coupled directly to the device 1, to illuminate the substantially transparent portions of the device 1 and thus allow the operator to see the body cavity or tract opened by the device 1.

When the device 1 is in a "closed" position and ready to be inserted into a body opening (e.g., as shown in FIGS. 1A–D, and the left-hand side of FIG. 7), the first and second head halves 2a and 2b define a substantially conical surface with an open base 20. In the embodiment of the invention shown in FIGS. 1A–C, 2A, 3B, and 7, the outer surface o of the first and second head halves 2a and 2b is generally convex and the inner surface i of the first and second head halves 2a and 2b is generally concave. As used herein, "substantially conical" includes any surface which circumscribes a lumen with a continuously varying internal diameter.

In the embodiment of the invention shown in FIG. 1D, each half of the head 2 may be divided into four basic elements which contribute to the head 2's substantially conical surface: half of a semicircular ridge 5 which is the point of coupling for one of the handle portions (3a or 3b) of the handle 3 and which forms the base of the conical surface; half of a first frustoconical portion 6 which is proximal to the semicircular ridge 5; half of a second frustoconical portion 7 adjacent to the first frustoconical portion 6; and half of a tip portion 8, located at the distal insertion end of the head portion 2. The first frustoconical portion 6 is generally wider in radius than the second frustoconical portion 7. A head half and respective handle portion may be molded as a single piece, being integral with a respective handle portion; alternatively, a head half may be attached or fused to a handle piece which is molded separately.

Figure 5A:
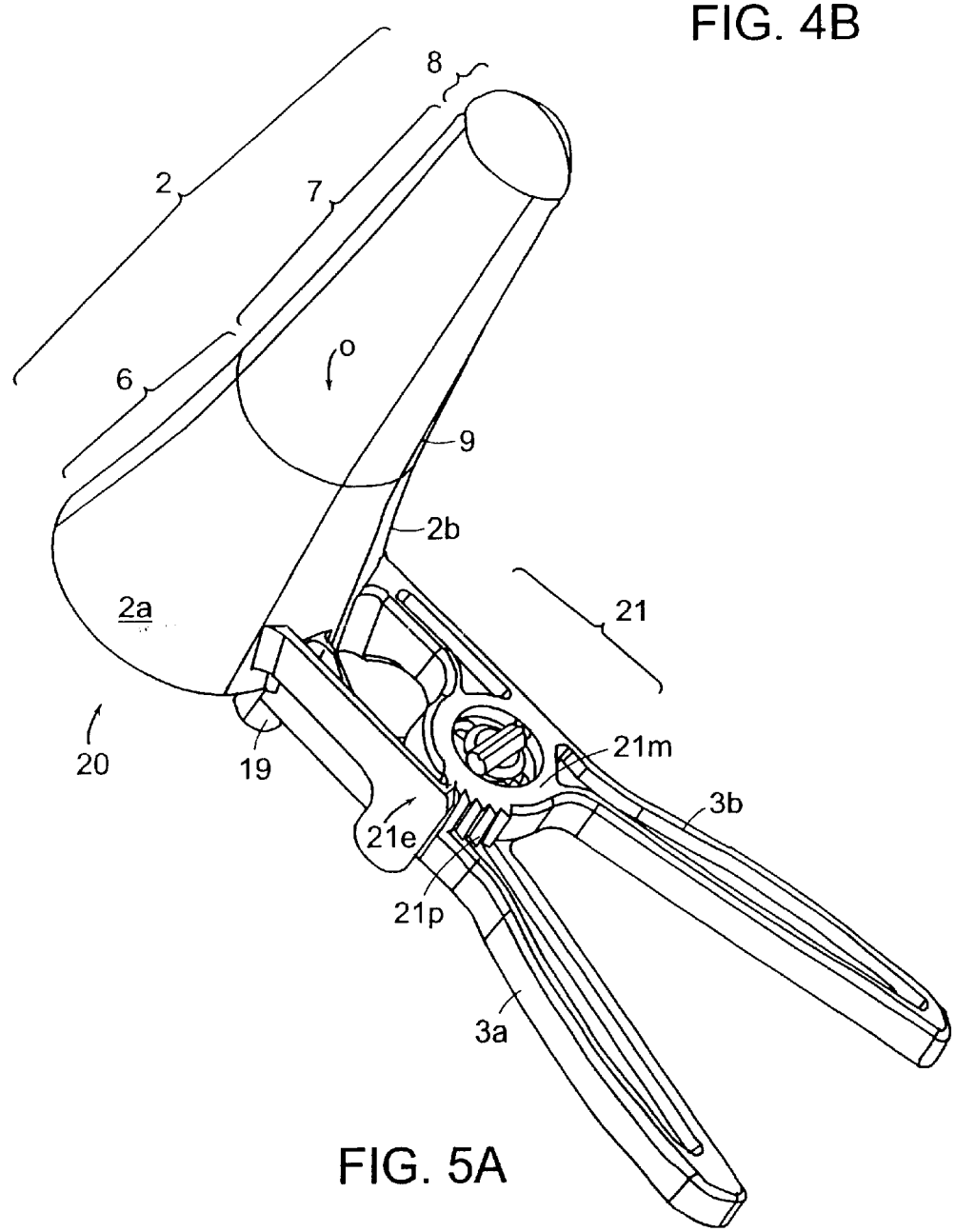
FIG. 5A shows a perspective view of an embodiment of the invention in which a locking mechanism is provided as part of the hinge assembly of the retractor/speculum device.
Figure 5B:
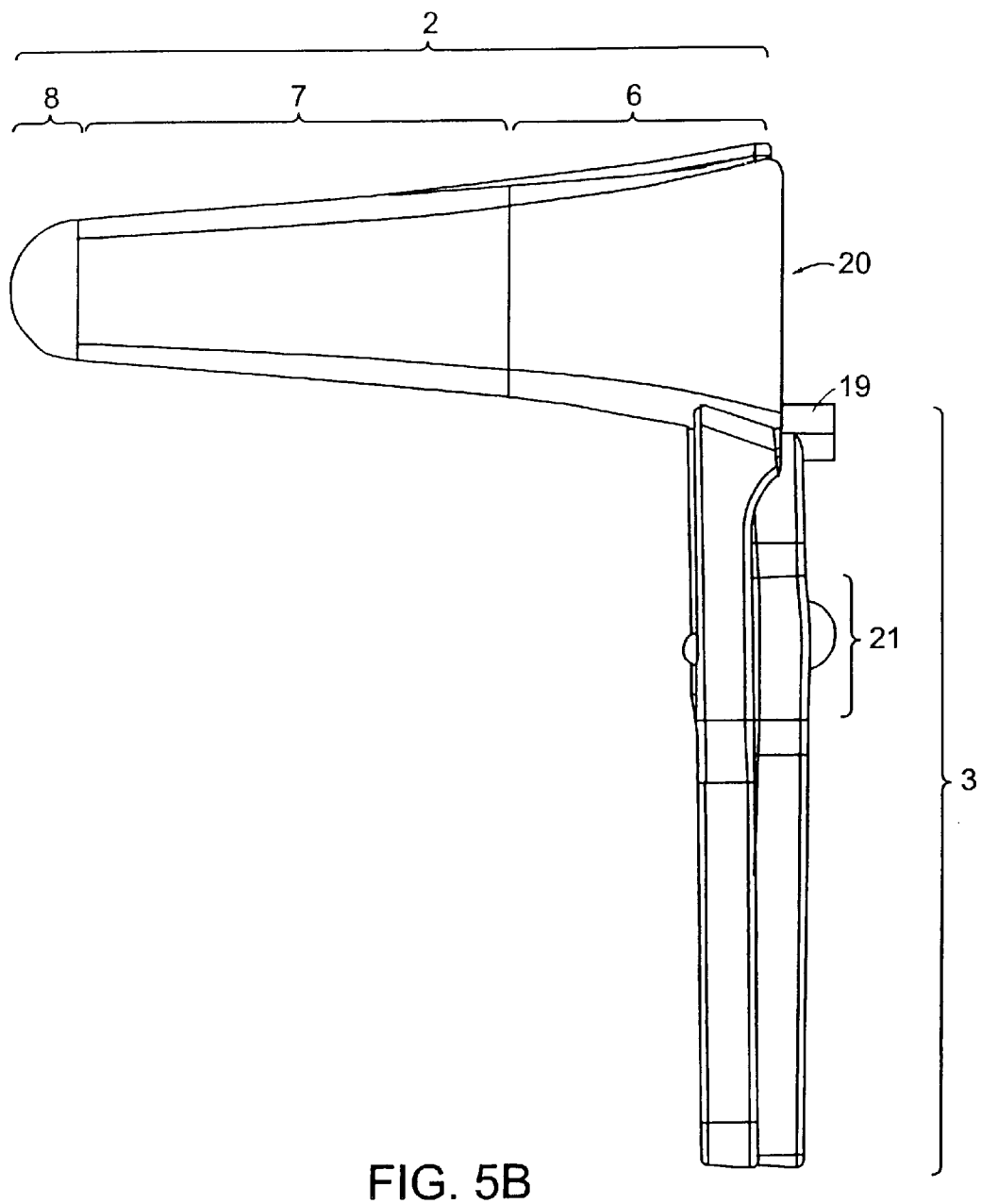
FIG. 5B shows a side view of this embodiment.

In a further embodiment of the invention, as shown in FIGS. 5A and 5B, a discrete semicircular ridge 5 may not be present and the handle portions 3a and 3b may be attached directly to the respective halves of frustoconical portion 6.

Figure 1A:
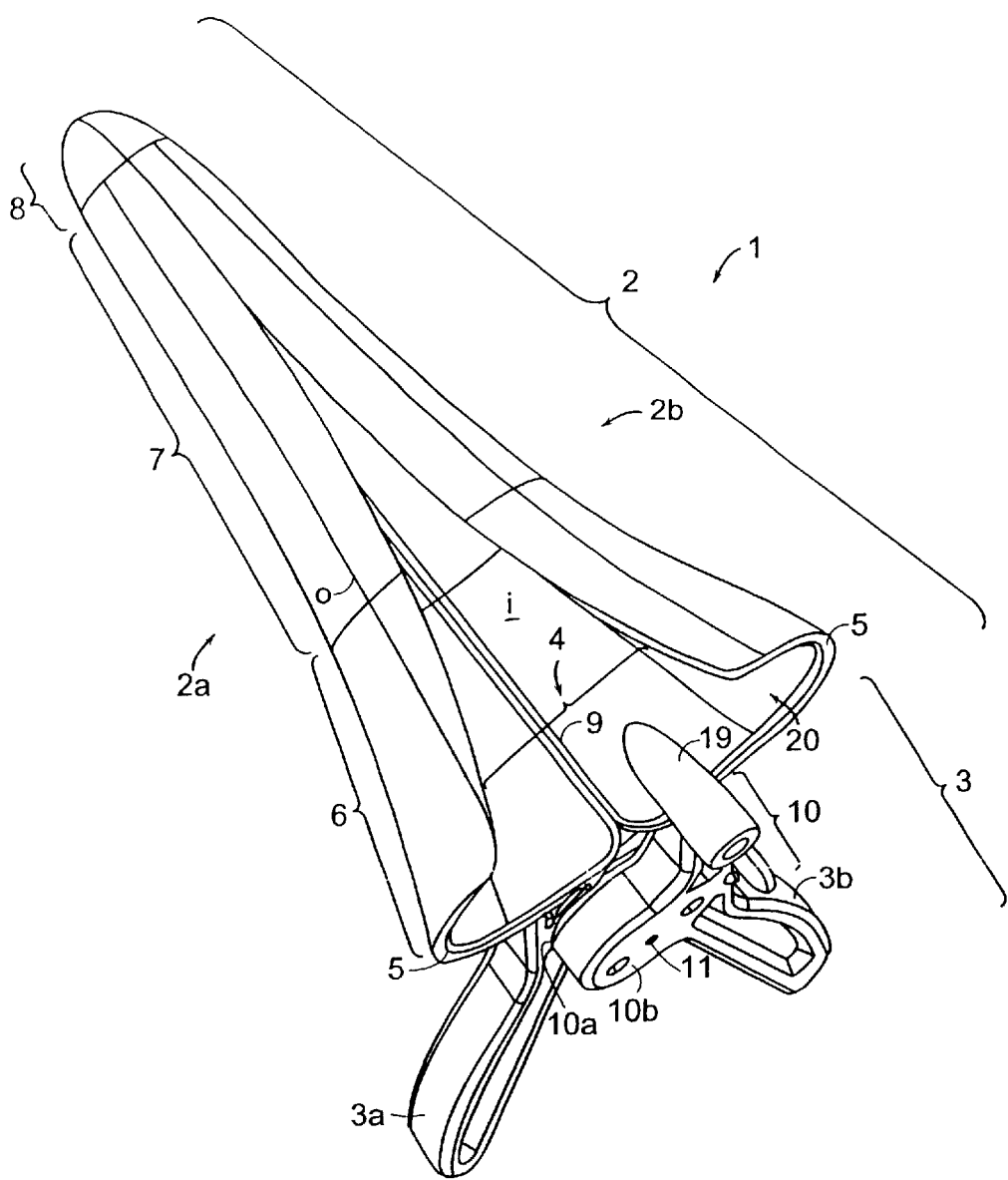
Figure 1B:
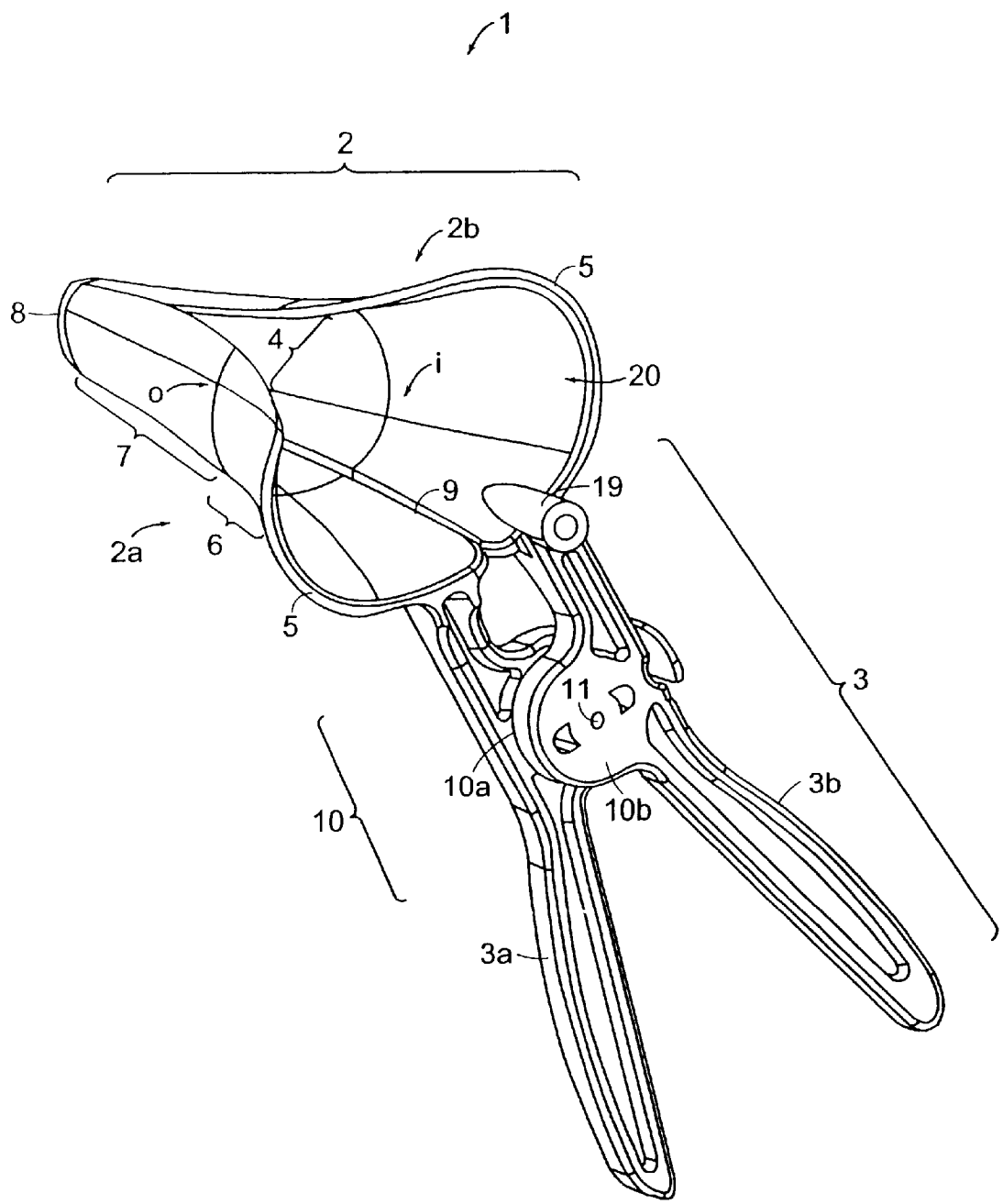
Figure 1C:
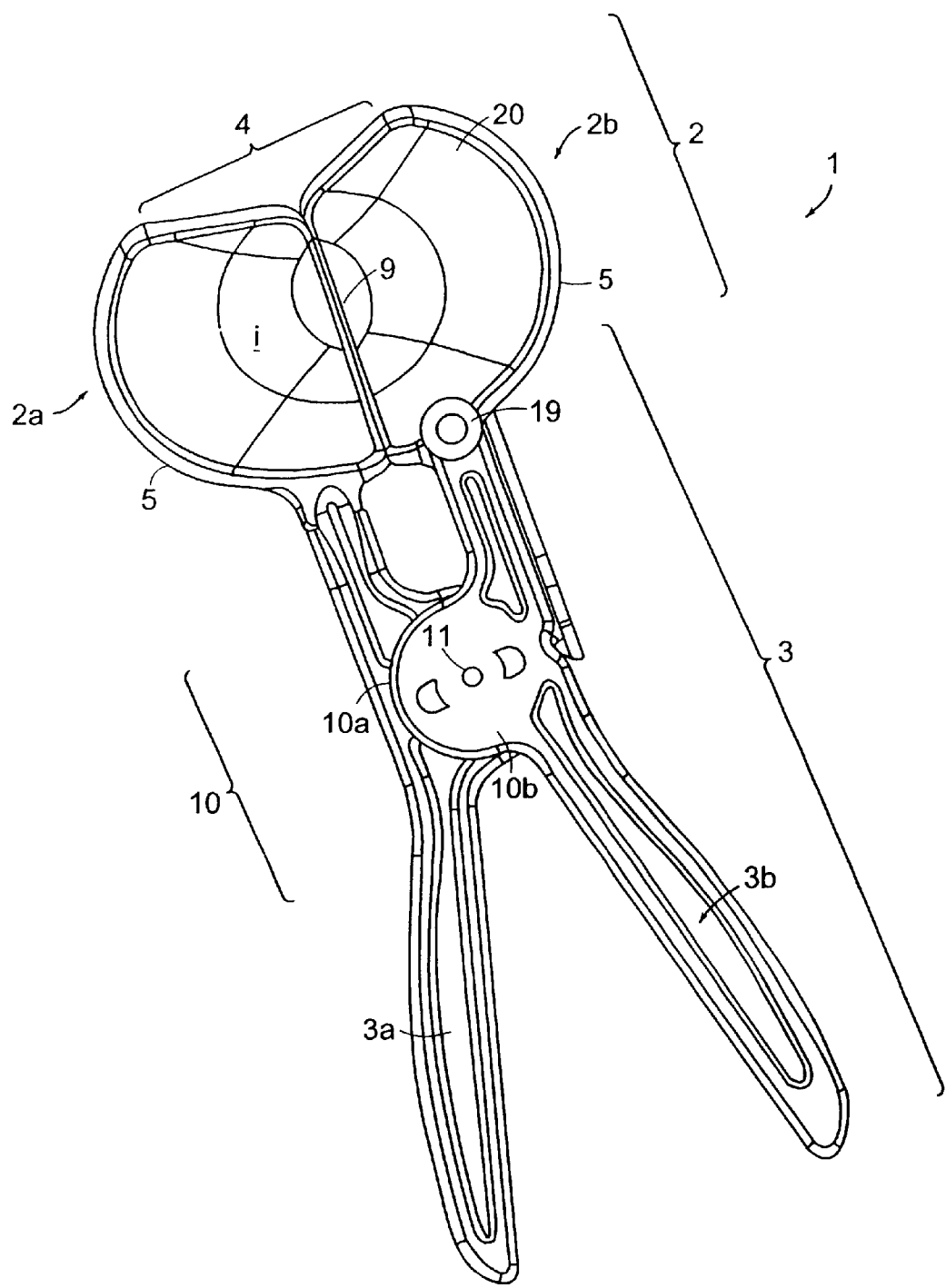

When the device 1 is in a closed position, as shown in FIGS. 1A–D and the left-hand side of FIG. 7, the first and second head halves 2a and 2b are in close proximity. As shown in FIG. 1D, for example, the first head half 2a and the second head half 2b contact each other along a midline 9 along the lower surface of the head 2. In contrast, the upper surface of both the first frustoconical portion 6 and the second frustoconical portion 7 are partially "cut-away" such that when the two halves of the head are in close proximity, the upper surface of the head 2 comprises a gap 4.

Figure 2A:
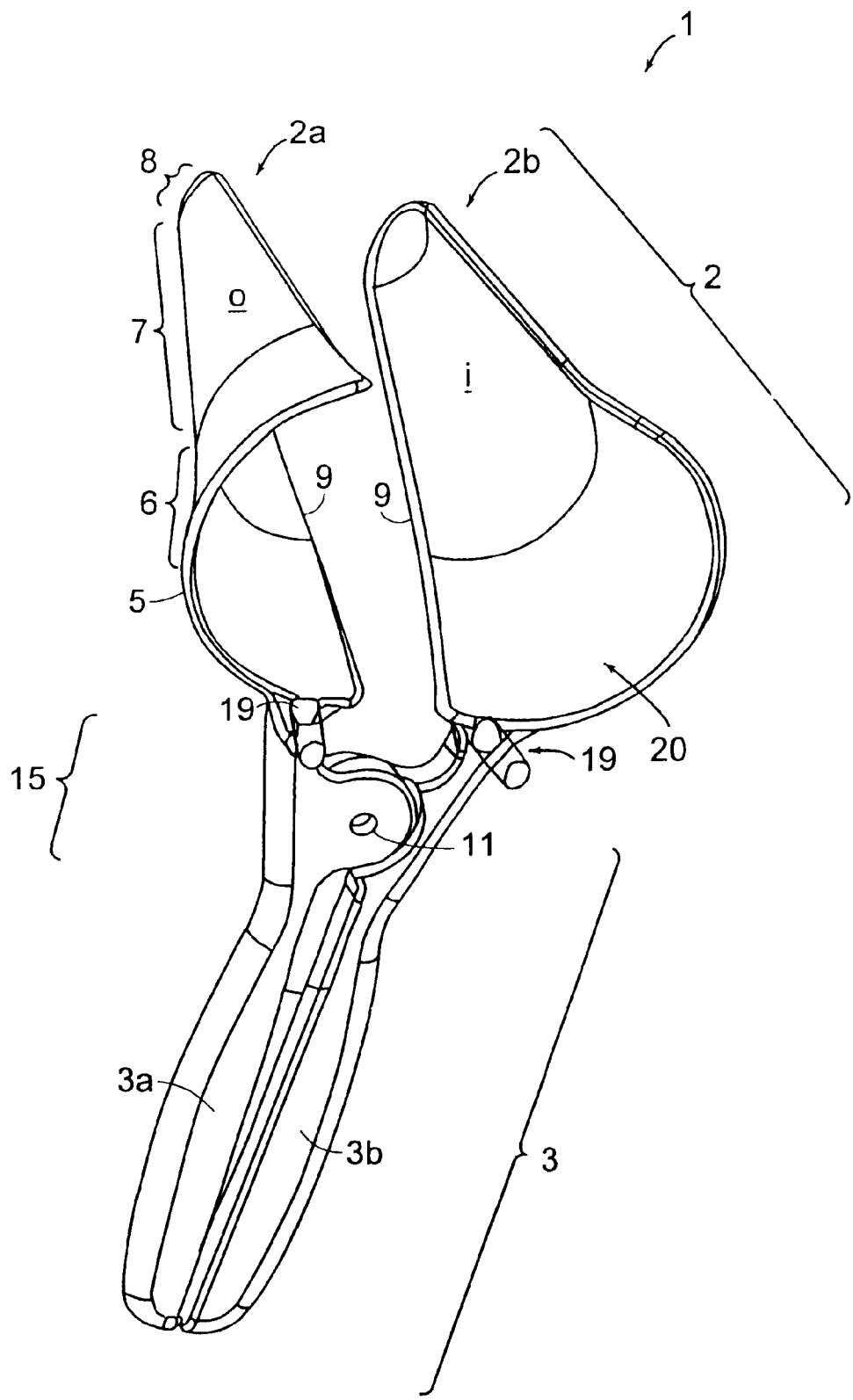
FIGS. 2A and 2B show perspective views of a retractor/speculum device in an open position according to one embodiment of the invention.
Figure 2B:
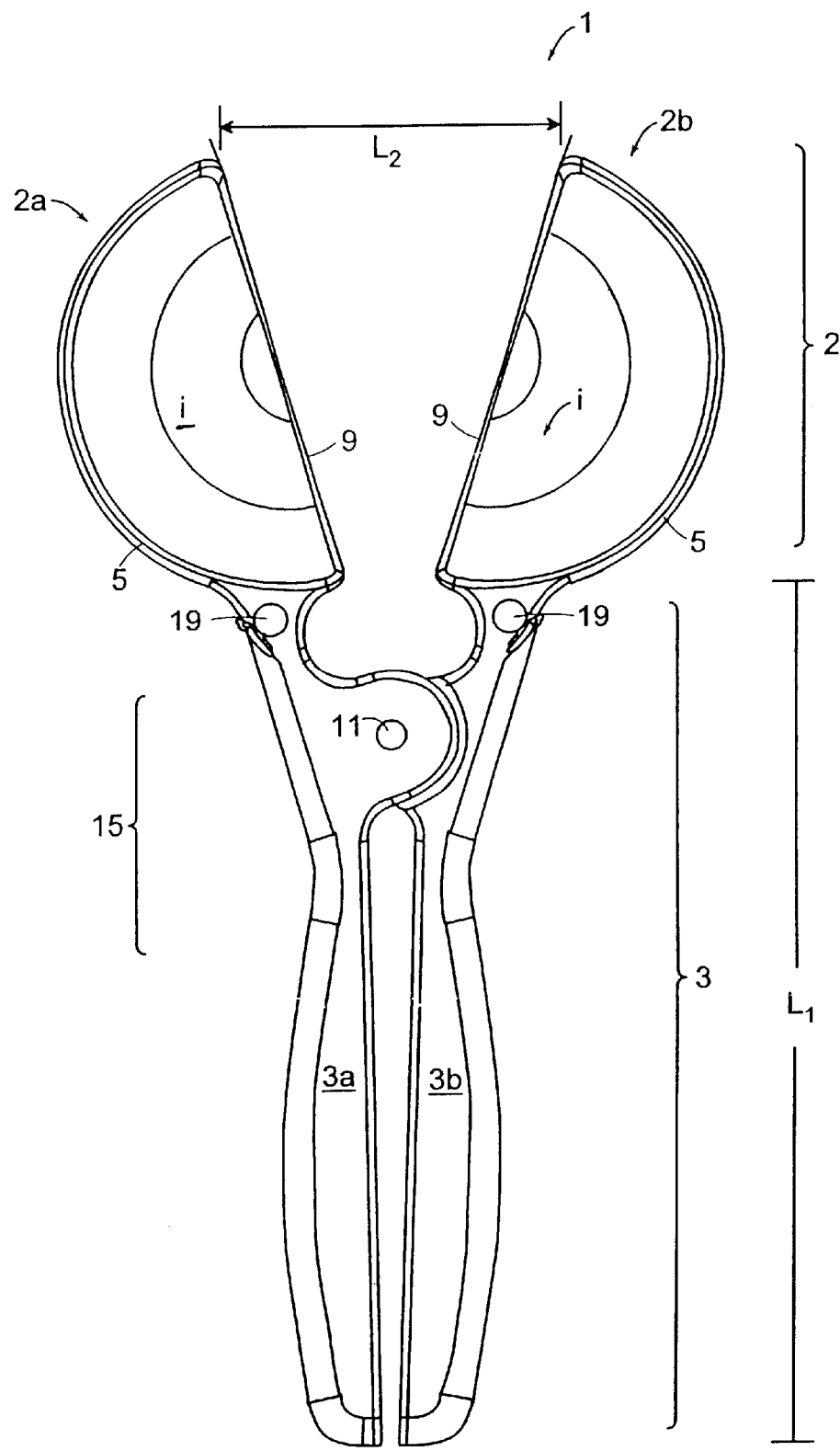
Figure 3A:
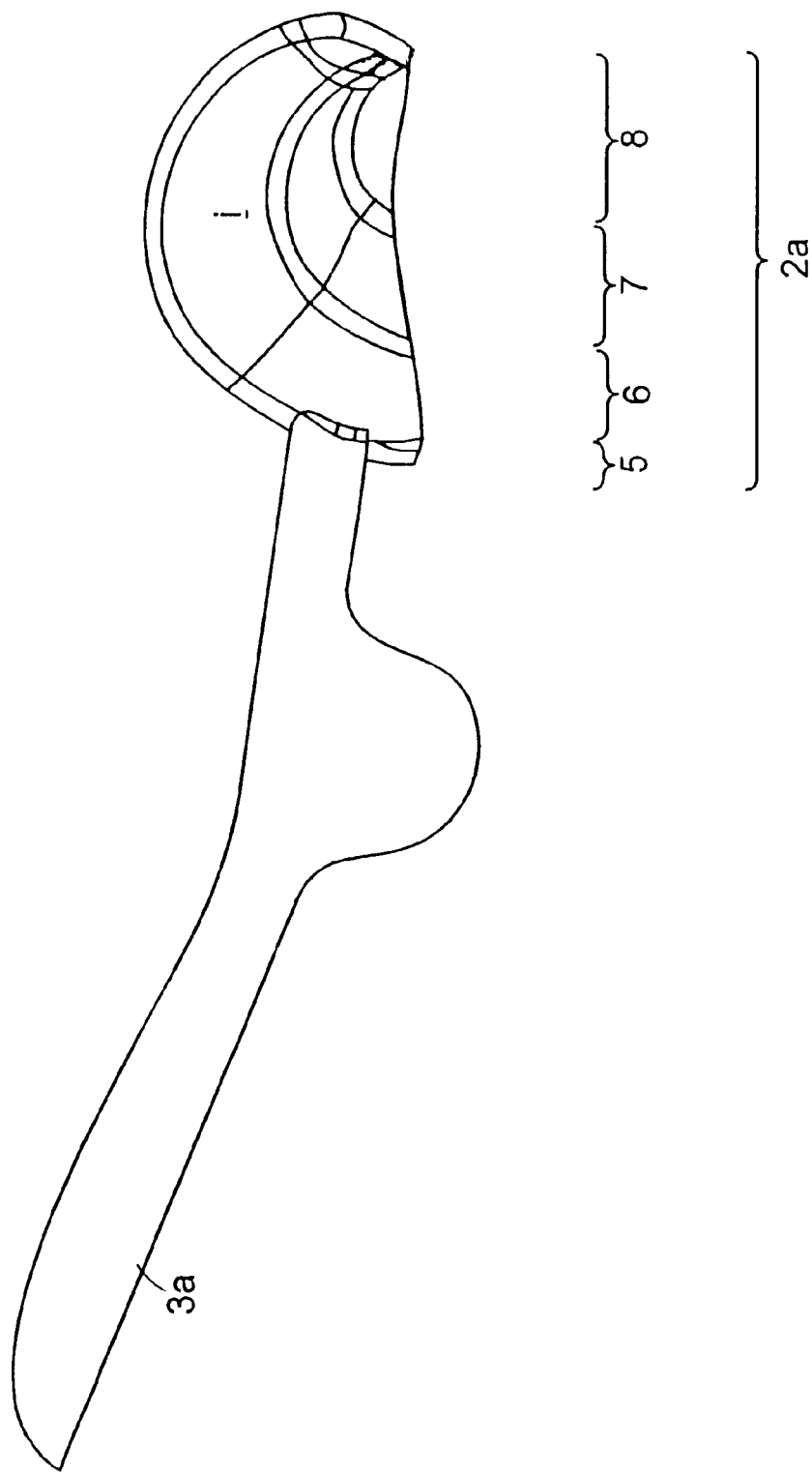
FIG. 3A is a back view of one half of the retractor/speculum of FIG. 1.
Figure 3B:
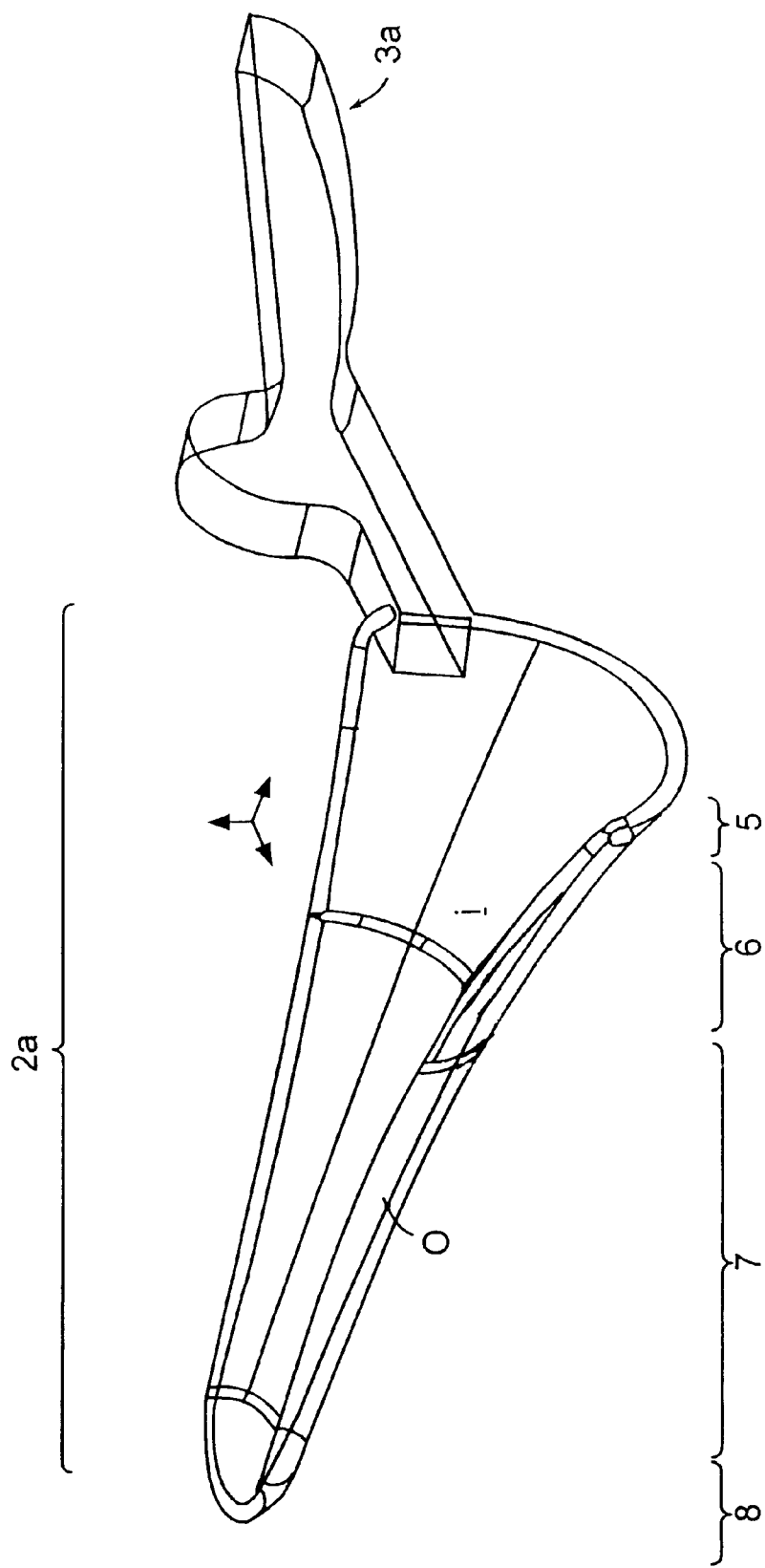
FIG. 3B is a perspective view of the half shown in FIG. 3A.

Once in the body opening, actuation of the handle portions 3a and 3b of the handle 3 causes the first and second head halves 2a and 2b to splay apart (e.g., as shown in FIGS. 2A and 2B and in the right-hand side of FIG. 7), thereby enlarging the body opening. In the "open" or splayed-apart position, the gap 4 in the head 2 enlarges. This enlarged gap 4, together with opening 20 at the base of the head 2, provides an area of access that allows the operator to insert one or more fingers into the body cavity and inspect the body cavity tactily at least near the gap 4. The gap 4 also provides the operator with the ability to insert a variety of medical instruments into the body cavity, for example a suturing mechanism. The device 1 may be opened completely or may be opened to an intermediary position, depending upon the amount of clearance required.

The handle 3 of the device 1 comprises two halves, namely, handle portion 3a and 3b. In the embodiment of the invention shown in FIGS. 1A–C, the two handle portions 3a and 3b join at a hinge assembly 10. As shown in an enlarged view in FIGS. 6A and 6B, hinge assembly 10 comprises hinge elements 10a and 10b, which are extensions of handle portions 3a and 3b, respectively, and comprise complementary shapes. Hinge elements 10a and 10b are connected at a pivot point 11. The hinge elements 10a and 10b may have coupling elements, such as mating plastic elements 12a and 12b, respectively, that snap together to form the pivot point 11 (FIG. 6A). Alternatively, the hinge elements 10a and 10b can be joined by a bolt or rod 13 inserted at a hole 14 that runs through each hinge element 10a and 10b (FIG. 6B). In this embodiment of the invention, the bolt or rod 13 may be secured by a nut or pin.

In another embodiment of the invention, shown in FIGS. 2A and 2B, the two handle portions 3a and 3b join at a different type of hinge assembly 15. As shown in the enlarged view of hinge assembly 15 in FIG. 6C, one of the handle portions, in this example, 3b, comprises a first and second interconnection element 15u and 15l, while the other handle portion, in this example, 3a, comprises an inner interconnection element 15m. The inner interconnection element 15m is sandwiched, or interleaved, between the first and second outer interconnection elements 15u and 15l by a coupling element at pivot point 11. As with hinge assembly 10, discussed above, interconnection elements 15u, 15l, and 15m may be joined together by means of plastic mating elements 12a and 12b (as shown in FIG. 6C) or by a bolt or rod.

Figure 4A:
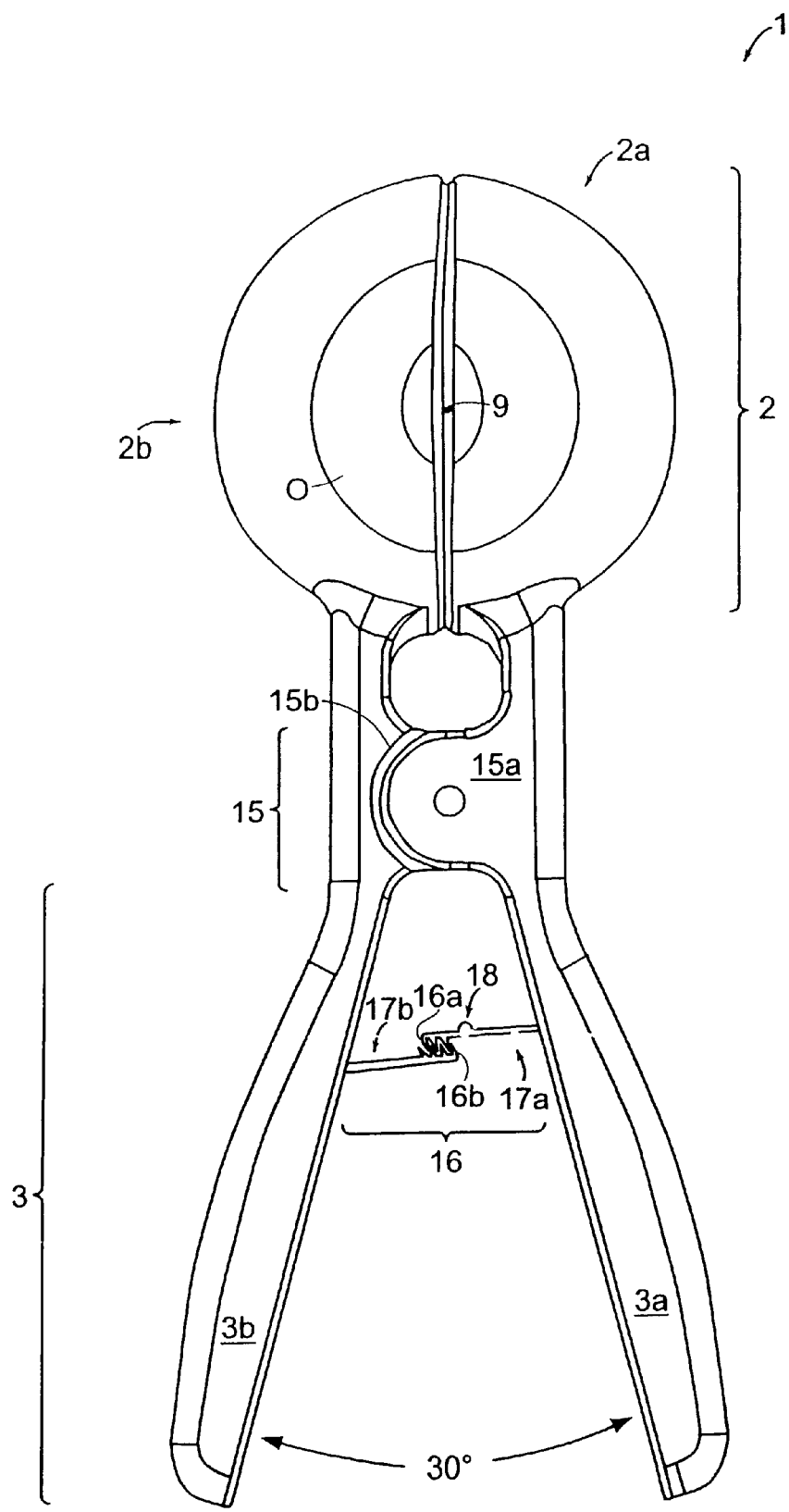
FIG. 4A shows the back of a retractor/speculum device according to one embodiment of the invention which includes a locking mechanism.
Figure 4B:
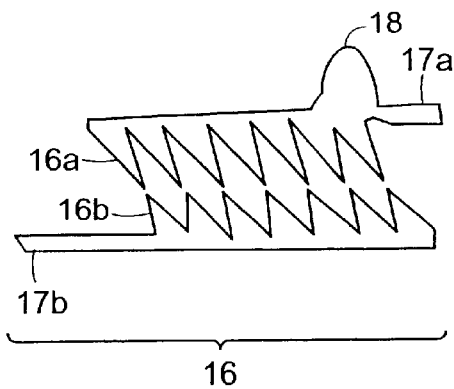
FIG. 4B shows an enlarged view of the locking mechanism of the device.

In the embodiment of the invention shown in FIGS. 4A and 4B, the handle 3 further comprises a locking mechanism 16. The locking mechanism comprises two sets 16a and 16b of resilient, evenly spaced lugs, each set projecting from the distal ends of first and second cross-bars 17a and 17b, which extend from handle portions 3a and 3b, respectively, in a direction generally perpendicular to the longitudinal axis of the handle 3. Cross-bars 17a and 17b are slightly offset from each other and the lugs at the distal end of one cross-bar point in an opposite direction to the lugs at the distal end of the other cross-bar such that both sets of lugs 16a and 16b can snap together to effectively lock the device. The locking mechanism 16 may be released by the operator applying a twisting action with one hand to the handle portions 3a and 3b thereby unsnapping the lugs. In a different embodiment of the invention, the operator may release the locking mechanism 16 by pushing down on a thumb tab 18 at the distal end of one of the cross-bars.

In another embodiment of the invention, an integrated locking mechanism/hinge assembly 21 is provided. As shown in FIG. 5A, one of the handle portions, in this example, 3b, may comprise a mating hinge element 21m which comprises a plurality of projections 21p. The other handle portion, in this example, 3a, comprises an engaging portion 21e, which is capable of meshing with one of the projections 21p of the mating hinge element 21m to lock the device in a selected position. It should be readily apparent to one of ordinary skill in the art that the mating hinge element 21m may be configured to comprise any number and arrangement of projections 21p, so long as the position of the projections 21p relative to the engaging portion 21e changes upon movement of the handle portions, 3a and 3b, to restrict further movement of the handle 3. In one embodiment of the invention, manipulation of the handle portions 3a and 3b with the single hand of an operator can engage this locking mechanism.

The orientation of the handle 3 relative to the head 2 of the device 1 may be varied to provide an operator with freer access to a body opening. In the embodiment of the invention shown in FIGS. 1A–C, 2A–B, 3A–B, 4A, 5A–B, and 7, the handle portions 3a and 3b of the handle 3 are disposed substantially perpendicular to the two halves 2a and 2b, respectively, of the head 2. This arrangement allows the operator to have access to the head 2 and the body cavity in which the head 2 is inserted without interference from the two handle portions 3a and 3b. As defined herein, "substantially perpendicular" refers to an orientation of the handle 3 relative to the head 2 in which the handle 3 is out of the line of sight of the body opening.

The two handle portions 3a and 3b of the handle 3 can also be oriented at other than 90 degrees from the two halves 2a and 2b of the head 2. In an alternative embodiment of the invention, the two handle portions 3a and 3b of the handle 3 can be oriented in the same plane as the longitudinal axis 23 of the head 2 to a point on the handle 3 distal to a hinge assembly 10 or 15. The two handle portions 3a and 3b of the handle 3 could then angle downward in a direction away from the opening 20 at the base of the head 2. In the embodiment of the invention shown in FIG. 4A, the two handle portions 3a and 3b of the handle 3 have a 30 degree angle of activation.

In another embodiment of the invention, a fixture or socket 19 for receiving one or more light-transmitting fiber optic lines or cables or a light source can be disposed on the semicircular ridge 5 (or on the rim of frustoconical portion 6 when there is no ridge) of one or both halves 2a and 2b of the head 2. As shown in FIG. 1D, the socket(s) 19 can be cylindrical-shaped with a ribbon element 22 that retains the cable(s) or the light source, preferably by a collapsible friction fit. The shape and size of the socket(s) 19 can be complementary to any fiber optic light cable(s) or light source that is known in the art. Also, the socket(s) 19 can be located elsewhere, such as on handle portion 3a and/or 3b. Because of the substantially transparent nature of the device 1, the cable(s) or light source provides a means to illuminate the device 1 and allow the operator to see into the body cavity being retracted without the need for an external light being shined into the body cavity by an individual assisting the operator. In a further embodiment of the invention, when the longitudinal axis of the handle 3 extends substantially perpendicularly from the head 2 of the device 1, only the head 2 of the device 1 need be substantially transparent.

It should be readily apparent to those of ordinary skill in the art that the exact dimensions of the different components of the device 1 can be varied depending on the nature of the opening being retracted. In one embodiment, such as the embodiment shown in FIG. 2B, the dimensions of the device 1 can be as follows: L1 can be approximately 8 inches and L2 can be approximately 2 inches. In the embodiment of the invention shown in FIG. 1D, the dimensions of the device 1 can be as follows: L3 can be approximately 1 inch, L4 can be approximately 1 ⅝ inches, L5 can be approximately 3 inches, and L6 can be approximately 5 inches. Having thus described certain embodiments of the present invention, various alterations, modifications, and improvements will be apparent to those skilled in the art. Such variations, modifications, and improvements are intended to be within the spirit and scope of the invention. The materials employed, as well as their shapes and dimensions, generally can vary. Accordingly, the foregoing description is by way of example only and is not intended to be limiting.

What is claimed is:

1. A medical device, comprising:
   a substantially transparent head having a longitudinal axis and defining a substantially conical surface, an internal space, an opening at a base of the head, and a gap disposed at an upper surface of the head, the head comprising a first head half and a second head half, the first and second head halves being substantially symmetrical and contacting each other at least along a lower surface of the head when the head is in a closed position, the gap defined by portions of the first and second head halves that do not contact each other at the upper surface when the head is in the closed position; and
   a handle coupled to the lower surface of the head near the base of the head and extending substantially perpendicular to the length of the head, actuation of the handle causing angular motion of the first and second head halves about the longitudinal axis away from or toward each other, such that angular motion of the head halves away from each other to an open position enlarges the gap, the gap and the opening at the base of the head allowing an operator to insert one or more fingers into the internal space of the head at least when the head is in the open position.

2. The medical device of claim 1 wherein at least one of the first and second head halves comprises a socket for accepting a light source.

3. The medical device of claim 1 wherein the handle comprises a first handle portion and a second handle portion.

4. The medical device of claim 3 wherein at least one of the first and second handle portions comprises a socket for accepting a light source.

5. The medical device of claim 3 wherein the first handle portion extends substantially perpendicularly from the first head half and the second handle portion extends substantially perpendicularly from the second head half.

6. The medical device of claim 5 wherein the first handle portion is formed integrally with the first head half and the second handle portion is formed integrally with the second head half.

7. The medical device of claim 1 further comprising a socket for accepting a light source.

8. The medical device of claim 7 wherein the socket is disposed at the base of the head.

9. The medical device of claim 7 wherein the socket and handle are located to provide a line of sight to a body cavity of a patient that allows the operator to view the body cavity when at least a portion of the head of the device is inserted into the body cavity.

10. A method of using a medical device, comprising:

providing the device which comprises a substantially transparent head having a longitudinal axis and defining a substantially conical surface, an internal space, an opening at a base of the head, and a gap disposed at an upper surface of the head, the head comprising a first head half and a second head half, the first and second head halves being substantially symmetrical and contacting each other at least along a lower surface of the head when the head is in a closed position, the gap defined by portions of the first and second head halves that do not contact each other at the upper surface when the head is in the closed position, a handle coupled to the lower surface of the head near the base of the head and extending substantially perpendicular to the length of the head, actuation of the handle causing angular motion of the first and second head halves about the longitudinal axis away from or toward each other, such that angular motion of the head halves away from each other enlarges the gap, the gap and the opening at the base of the head allowing an operator to insert one or more fingers into the internal space of the head at least when the head is in the open position, and a socket for accepting a light source;

inserting at least a portion of the head of the device into a body cavity of a patient; and illuminating at least the head of the device by providing a source of light to the socket of the device.

* * * * *